(12) United States Patent
Lozier et al.

(10) Patent No.: US 10,966,704 B2
(45) Date of Patent: Apr. 6, 2021

(54) METHODS AND SYSTEMS FOR STITCHING SOFT TISSUE TO BONE

(71) Applicant: Biomet Sports Medicine, LLC, Warsaw, IN (US)

(72) Inventors: Antony J. Lozier, Warsaw, IN (US); Matthew Prygoski, Warsaw, IN (US); Daniel P. Murphy, Warsaw, IN (US); Hallie E. Brinkerhuff, Warsaw, IN (US); Michael Giordano, Osceola, IN (US); J. Craig Fryman, New Paris, IN (US); Alex McMullen, Plain City, OH (US); Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 432 days.

(21) Appl. No.: 15/808,547

(22) Filed: Nov. 9, 2017

(65) Prior Publication Data

US 2018/0125475 A1    May 10, 2018

Related U.S. Application Data

(60) Provisional application No. 62/419,823, filed on Nov. 9, 2016.

(51) Int. Cl.
*A61B 17/04* (2006.01)
*A61B 17/06* (2006.01)
(Continued)

(52) U.S. Cl.
CPC ...... *A61B 17/0401* (2013.01); *A61B 17/0483* (2013.01); *A61B 17/06166* (2013.01);
(Continued)

(58) Field of Classification Search
CPC ............ A61B 17/0401; A61B 17/0483; A61B 17/06166; A61B 17/0487; A61B 17/0642;
(Continued)

(56) References Cited

U.S. PATENT DOCUMENTS 3,584,629 A     6/1971  Hoef et al.
3,618,842 A    11/1971  Bryan
(Continued)

FOREIGN PATENT DOCUMENTS

CN         86100996 A     9/1986
CN         2145361 Y     11/1993
(Continued)

OTHER PUBLICATIONS

U.S. Appl. No. 12/787,518 U.S. Pat. No. 8,221,433, filed May 26, 2010, Bone Fixation Tool.
(Continued)

*Primary Examiner* — Katherine M Rodjom
(74) *Attorney, Agent, or Firm* — Schwegman Lundberg & Woessner, P.A.

(57) ABSTRACT

Disclosed are systems and methods for performing soft tissue repair by delivering a suture through the soft tissue and underlying bone at two or more fixation points that can be spaced apart from each other and connected by the suture on the surface of the soft tissue. The two or more fixation points and the suture connected there between can be a continuous strand of suture, which can form a stitching assembly that can provide sufficient fixation in the bone and minimize disruption to the soft tissue and bone. In an example, the suture can be delivered into the bone using one or more implants that can catch the suture to drive the suture through the tissue and into the bone. The one or more implants can include structural features to aid in securing the suture to the implant. In an example, the suture can include
(Continued)

structural features or be formed of a material to aid in fixation of the suture in the bone.

11 Claims, 10 Drawing Sheets

(51) Int. Cl.
    *A61F 2/08*     (2006.01)
    *A61B 17/064*     (2006.01)
    *A61B 17/00*     (2006.01)

(52) U.S. Cl.
    CPC ......... *A61F 2/0811* (2013.01); *A61B 17/0482* (2013.01); *A61B 17/0487* (2013.01); *A61B 17/0642* (2013.01); *A61B 17/06123* (2013.01); *A61B 2017/00544* (2013.01); *A61B 2017/0403* (2013.01); *A61B 2017/0409* (2013.01); *A61B 2017/0414* (2013.01); *A61B 2017/0496* (2013.01); *A61B 2017/06052* (2013.01); *A61B 2017/06176* (2013.01); *A61B 2017/06185* (2013.01)

(58) Field of Classification Search
    CPC .. A61B 2017/06176; A61B 2017/0414; A61B 2017/06052; A61B 2017/0409; A61B 2017/0496; A61F 2/0811
    See application file for complete search history.

(56) References Cited

U.S. PATENT DOCUMENTS

| | | | |
|---|---|---|---|
| 3,662,939 A | 5/1972 | Bryan | |
| 3,752,161 A | 8/1973 | Bent | |
| 3,815,476 A | 6/1974 | Green et al. | |
| 3,842,839 A | 10/1974 | Mails et al. | |
| 3,905,276 A | 9/1975 | Noiles et al. | |
| 4,349,028 A | 9/1982 | Green | |
| 4,540,110 A | 9/1985 | Bent et al. | |
| 4,632,100 A | 12/1986 | Somers et al. | |
| 4,728,876 A | 3/1988 | Mongeon et al. | |
| 4,738,255 A | 4/1988 | Goble et al. | |
| 4,898,156 A | 2/1990 | Gatturna et al. | |
| 4,901,712 A | 2/1990 | Voegell et al. | |
| 4,909,419 A | 3/1990 | Yamada et al. | |
| 4,915,013 A | 4/1990 | Moraht et al. | |
| 4,938,408 A | 7/1990 | Bedi et al. | |
| 4,946,468 A | 8/1990 | Li | |
| 4,951,861 A | 8/1990 | Schulze et al. | |
| 5,002,550 A | 3/1991 | Li | |
| 5,041,129 A | 8/1991 | Hayhurst et al. | |
| 5,049,775 A | 9/1991 | Smits | |
| 5,080,273 A | 1/1992 | Meyer | |
| 5,100,417 A | 3/1992 | Cerier | |
| 5,102,421 A | 4/1992 | Anspach | |
| 5,125,923 A | 6/1992 | Tanner et al. | |
| 5,136,469 A | 8/1992 | Carusillo et al. | |
| 5,141,520 A | 8/1992 | Goble et al. | |
| 5,149,603 A | 9/1992 | Fleming et al. | |
| 5,160,795 A | 11/1992 | Milliman | |
| D331,463 S | 12/1992 | Rosenberg et al. | |
| 5,207,679 A | 5/1993 | Li | |
| 5,217,486 A | 6/1993 | Rice et al. | |
| 5,236,445 A | 8/1993 | Hayhurst et al. | |
| 5,258,016 A | 11/1993 | Dipoto et al. | |
| 5,265,582 A | 11/1993 | Bhogal | |
| 5,269,809 A | 12/1993 | Hayhurst et al. | |
| 5,324,308 A | 6/1994 | Pierce | |
| 5,330,487 A | 7/1994 | Thornton et al. | |
| 5,358,511 A | 10/1994 | Gatturna et al. | |
| 5,363,834 A | 11/1994 | Stuchlik | |
| 5,370,037 A | 12/1994 | Bauer et al. | |
| D356,154 S | 3/1995 | Ferragamo | |
| 5,398,861 A | 3/1995 | Green | |
| 5,400,536 A | 3/1995 | Milliman | |
| 5,403,348 A | 4/1995 | Bonutti | |
| 5,411,523 A | 5/1995 | Goble | |
| 5,415,631 A | 5/1995 | Churinetz et al. | |
| 5,431,322 A | 7/1995 | Green et al. | |
| 5,443,482 A | 8/1995 | Stone et al. | |
| 5,485,887 A | 1/1996 | Mandanis | |
| 5,486,197 A | 1/1996 | Le et al. | |
| 5,497,758 A | 3/1996 | Dobbins et al. | |
| 5,501,683 A | 3/1996 | Trott | |
| 5,515,838 A | 5/1996 | Anderson | |
| 5,522,844 A | 6/1996 | Johnson | |
| 5,569,306 A | 10/1996 | Thal | |
| 5,613,483 A | 3/1997 | Lukas et al. | |
| 5,628,444 A | 5/1997 | White | |
| 5,664,552 A | 9/1997 | Kunimoto | |
| 5,669,369 A | 9/1997 | Scott | |
| 5,687,897 A | 11/1997 | Fa et al. | |
| 5,704,150 A | 1/1998 | Milliman | |
| 5,709,334 A | 1/1998 | Sorrentino et al. | |
| 5,711,472 A | 1/1998 | Bryan | |
| 5,755,213 A | 5/1998 | Gardner, Jr. et al. | |
| 5,755,726 A | 5/1998 | Pratt et al. | |
| 5,769,781 A | 6/1998 | Chappuis | |
| 5,772,096 A | 6/1998 | Osuka et al. | |
| 5,775,312 A | 7/1998 | Wilkinson et al. | |
| 5,779,130 A | 7/1998 | Alesi et al. | |
| 5,782,821 A | 7/1998 | Couch | |
| 5,785,228 A | 7/1998 | Fa et al. | |
| 5,803,733 A | 9/1998 | Trott et al. | |
| 5,859,359 A | 1/1999 | Reid | |
| 5,862,972 A | 1/1999 | Green et al. | |
| 5,865,360 A | 2/1999 | White | |
| 5,878,734 A | 3/1999 | Johnson et al. | |
| 5,878,736 A | 3/1999 | Lotuaco, III | |
| 5,896,933 A | 4/1999 | White | |
| 5,913,303 A | 6/1999 | Kotsiopoulos | |
| 5,918,791 A | 7/1999 | Sorrentino et al. | |
| 5,924,413 A | 7/1999 | Johnson et al. | |
| 5,954,259 A | 9/1999 | Viola et al. | |
| 5,954,689 A | 9/1999 | Poulsen | |
| 5,957,119 A | 9/1999 | Perry et al. | |
| 5,957,951 A | 9/1999 | Cazaux et al. | |
| 5,989,214 A | 11/1999 | van de Wijdeven | |
| 5,997,500 A | 12/1999 | Cook et al. | |
| 6,006,704 A | 12/1999 | Phillips et al. | |
| 6,015,078 A | 1/2000 | Almeras et al. | |
| 6,016,945 A | 1/2000 | Phillips et al. | |
| 6,039,231 A | 3/2000 | White | |
| 6,059,749 A | 5/2000 | Marx | |
| 6,197,041 B1 | 3/2001 | Shichman et al. | |
| 6,223,658 B1 | 5/2001 | Rosa et al. | |
| 6,286,497 B1 | 9/2001 | Levkov | |
| 6,306,125 B1 | 10/2001 | Parker et al. | |
| 6,371,099 B1 | 4/2002 | Lee | |
| 6,371,348 B1 | 4/2002 | Canlas et al. | |
| 6,387,113 B1 | 5/2002 | Hawkins et al. | |
| 6,470,872 B1 | 10/2002 | Tiberius et al. | |
| 6,493,217 B1 | 12/2002 | Jenkins, Jr. | |
| 6,532,947 B1 | 3/2003 | Rosa et al. | |
| 6,578,565 B2 | 6/2003 | Casas Salva | |
| 6,613,011 B2 | 9/2003 | Castellano | |
| 6,620,135 B1 | 9/2003 | Weston et al. | |
| 6,766,795 B1 | 7/2004 | Sullivan | |
| 6,786,379 B2 | 9/2004 | Largo | |
| 6,851,447 B1 | 2/2005 | Carroll | |
| 6,877,647 B2 | 4/2005 | Green et al. | |
| 7,066,940 B2 | 6/2006 | Riedel et al. | |
| 7,069,922 B1 | 7/2006 | Orr | |
| 7,237,545 B2 | 7/2007 | Masse | |
| 7,320,687 B2 | 1/2008 | Lee | |
| 7,441,684 B2 | 10/2008 | Shelton, IV et al. | |
| 7,445,619 B2 | 11/2008 | Auge, II et al. | |
| 7,448,525 B2 | 11/2008 | Shelton, IV et al. | |
| 7,455,655 B2 | 11/2008 | Alexandre et al. | |
| 7,481,347 B2 | 1/2009 | Roy | |
| 7,601,165 B2 | 10/2009 | Stone | |
| 7,665,396 B1 | 2/2010 | Tippmann, Jr. | |
| 7,765,999 B1 | 8/2010 | Stephens et al. | |

(56) References Cited

U.S. PATENT DOCUMENTS

| | | |
|---|---|---|
| 7,780,701 B1 | 8/2010 | Meridew et al. |
| 8,221,433 B2 | 7/2012 | Lozier |
| 8,298,262 B2 | 10/2012 | Stone et al. |
| 8,603,102 B2 | 12/2013 | Lozier et al. |
| 8,828,052 B2 | 9/2014 | Caborn et al. |
| 8,852,202 B2 | 10/2014 | Lozier et al. |
| 9,987,067 B2 | 6/2018 | Giordano et al. |
| 2002/0165549 A1 | 11/2002 | Owusu-Akyaw et al. |
| 2003/0195498 A1 | 10/2003 | Treat et al. |
| 2003/0225411 A1 | 12/2003 | Miller |
| 2004/0068267 A1* | 4/2004 | Harvie .............. A61B 17/00491 606/92 |
| 2004/0144012 A1 | 7/2004 | Adams |
| 2004/0158196 A1 | 8/2004 | Garitano et al. |
| 2004/0189258 A1 | 9/2004 | Lehmann et al. |
| 2005/0010168 A1 | 1/2005 | Kendall |
| 2005/0096661 A1 | 5/2005 | Farrow et al. |
| 2005/0131414 A1 | 6/2005 | Chana |
| 2005/0159752 A1 | 7/2005 | Walker et al. |
| 2005/0165394 A1 | 7/2005 | Boyce et al. |
| 2005/0188973 A1 | 9/2005 | Monks |
| 2005/0188977 A1 | 9/2005 | Wygant |
| 2006/0124118 A1 | 6/2006 | Dobbins |
| 2006/0217729 A1 | 9/2006 | Eskridge et al. |
| 2006/0241589 A1 | 10/2006 | Heim et al. |
| 2006/0293648 A1 | 12/2006 | Herzon |
| 2007/0017497 A1 | 1/2007 | Masse |
| 2007/0169765 A1 | 7/2007 | Forster et al. |
| 2007/0175465 A1 | 8/2007 | Quinn et al. |
| 2007/0233133 A1 | 10/2007 | Cohen et al. |
| 2007/0235014 A1 | 10/2007 | Tiberius et al. |
| 2007/0270784 A1 | 11/2007 | Smith et al. |
| 2008/0015630 A1 | 1/2008 | Rousso |
| 2008/0029573 A1 | 2/2008 | Shelton et al. |
| 2008/0058820 A1 | 3/2008 | Harp |
| 2008/0103355 A1 | 5/2008 | Boyden et al. |
| 2008/0135598 A1 | 6/2008 | Burke et al. |
| 2008/0221580 A1 | 9/2008 | Miller et al. |
| 2008/0228104 A1 | 9/2008 | Uber et al. |
| 2008/0251569 A1 | 10/2008 | Smith et al. |
| 2008/0255607 A1 | 10/2008 | Zamlok |
| 2008/0269754 A1 | 10/2008 | Lutz et al. |
| 2008/0272172 A1 | 11/2008 | Zemlok et al. |
| 2008/0281343 A1 | 11/2008 | Dewey et al. |
| 2008/0281353 A1 | 11/2008 | Aranyi et al. |
| 2008/0283570 A1 | 11/2008 | Boyden et al. |
| 2008/0283574 A1 | 11/2008 | Boyden et al. |
| 2008/0283577 A1 | 11/2008 | Boyden et al. |
| 2008/0294024 A1 | 11/2008 | Cosentino et al. |
| 2008/0296346 A1 | 12/2008 | Shelton, IV et al. |
| 2009/0018548 A1 | 1/2009 | Charles |
| 2009/0032003 A1 | 2/2009 | Masse |
| 2009/0032568 A1 | 2/2009 | Viola et al. |
| 2009/0082715 A1 | 3/2009 | Charles |
| 2009/0090763 A1 | 4/2009 | Zemlok et al. |
| 2009/0108048 A1 | 4/2009 | Zemlok et al. |
| 2009/0108049 A1 | 4/2009 | Roy |
| 2009/0112243 A1 | 4/2009 | Boyden et al. |
| 2009/0118738 A1 | 5/2009 | Gerondale |
| 2009/0163943 A1 | 6/2009 | Cavanaugh et al. |
| 2009/0171354 A1 | 7/2009 | Deville et al. |
| 2009/0206136 A1 | 8/2009 | Moore et al. |
| 2009/0209990 A1 | 8/2009 | Yates et al. |
| 2009/0235910 A1 | 9/2009 | Maeda |
| 2009/0240245 A1 | 9/2009 | Deville et al. |
| 2009/0241931 A1 | 10/2009 | Masse |
| 2009/0259220 A1 | 10/2009 | Appling et al. |
| 2009/0264893 A1 | 10/2009 | Beale et al. |
| 2009/0264940 A1 | 10/2009 | Beale et al. |
| 2009/0270834 A1 | 10/2009 | Nisato et al. |
| 2009/0299359 A1 | 12/2009 | Swain |
| 2010/0012698 A1 | 1/2010 | Liang et al. |
| 2010/0024791 A1 | 2/2010 | Romney |
| 2010/0030205 A1 | 2/2010 | Herzon |
| 2010/0036391 A1 | 2/2010 | Zaleski et al. |
| 2010/0069943 A1 | 3/2010 | Roe |
| 2010/0076455 A1 | 3/2010 | Birkenbach et al. |
| 2010/0126486 A1 | 5/2010 | Halmone et al. |
| 2010/0154767 A1 | 6/2010 | Masse |
| 2012/0253411 A1 | 10/2012 | Lozier et al. |
| 2013/0116730 A1 | 5/2013 | Denham |
| 2014/0074127 A1 | 3/2014 | Giordano et al. |
| 2014/0094863 A1 | 4/2014 | Lozier et al. |
| 2014/0277126 A1* | 9/2014 | Burki ................. A61B 17/0401 606/232 |
| 2015/0250470 A1* | 9/2015 | Vargas ............... A61B 17/0401 606/232 |

FOREIGN PATENT DOCUMENTS

| | | |
|---|---|---|
| CN | 2153482 Y | 1/1994 |
| EP | 0171967 A2 | 2/1986 |
| EP | 0171967 A3 | 2/1986 |
| EP | 1859749 A2 | 11/2007 |
| WO | WO-9522934 A1 | 8/1995 |
| WO | WO-2010138538 A1 | 12/2010 |
| WO | WO-2014011841 A1 | 1/2014 |

OTHER PUBLICATIONS

U.S. Appl. No. 13/493,200 U.S. Pat. No. 8,603,102, filed Jun. 11, 2012, Bone Fixation Tool.

U.S. Appl. No. 14/098,877 U.S. Pat. No. 8,852,202, filed Dec. 6, 2013, Bone Fixation Tool.

"3M Staplizer Powered Metaphyse", [Online]. Retrieved from the Internet: <URL: http://www.wemed1.com/Products/spec.asp?ItemNumber=OR-3M-T100&Code=zzor3mc100>, (Accessed Apr. 22, 2013), 1 pg.

"U.S. Appl. No. 12/787,518, Notice of Allowance dated Apr. 26, 2012", 12 pgs.

"U.S. Appl. No. 12/787,518, Response filed Jan. 30, 2012 to Restriction Requirement dated Jan. 3, 2012", 2 pgs.

"U.S. Appl. No. 12/787,518, Restriction Requirement dated Jan. 3, 2012", 6 pgs.

"U.S. Appl. No. 13/493,200, Notice of Allowance dated Aug. 7, 2013", 11 pgs.

"U.S. Appl. No. 13/493,200, Response filed Jul. 3, 2013 to Restriction Requirement dated Jun. 5, 2013", 6 pgs.

"U.S. Appl. No. 13/493,200, Restriction Requirement dated Jun. 5, 2013", 8 pgs.

"U.S. Appl. No. 14/098,877, Notice of Allowance dated Jun. 4, 2014", 9 pgs.

"U.S. Appl. No. 14/098,877, Preliminary Amendment filed Jan. 23, 2014", 7 pgs.

"U.S. Appl. No. 14/098,877, Response filed May 19, 2014 to Restriction Requirement dated Apr. 17, 2014", 8 pgs.

"U.S. Appl. No. 14/098,877, Restriction Requirement dated Apr. 17, 2014", (Apr. 17, 2014), 8 pages.

"Chinese Application Serial No. 201080022735.4, Office Action dated Nov. 20, 2013", with English translation, 42 pages.

"Chinese Application Serial No. 201080022735.4, Response filed Apr. 4, 2014 to Office Action dated Nov. 20, 2013", with English claims, 14 pages.

"European Application Serial No. 10727219.7, Office Action dated Feb. 3, 2012", 2 pgs.

"European Application Serial No. 10727219.7, Office Action dated Mar. 26, 2012", 1 pg.

"European Application Serial No. 10727219.7, Response filed Aug. 10, 2012 to Office Action dated Feb. 3, 2012", 12 pgs.

"International Application Serial No. PCT/US2010/036126, International Preliminary Report on Patentability dated Dec. 8, 2011", 6 pgs.

"International Application Serial No. PCT/US2010/036126, International Search Report and Written Opinion dated Sep. 13, 2010", 10 pgs.

"Polysorb Meniscal Stapler XLS Device", [Online]. Retrieved from the Internet: <URL: http://www.sportssurgery.com/sportsmedicine/pageBuilderaspx?topicID=31604>, (2008), 1 pg.

(56) References Cited

OTHER PUBLICATIONS

"Repairing Fractured Bones by Use of Bioabsorbable Composites", Langley Research Center, Tech Briefs, [Online]. Retrieved from the Internet: <http://www.techbriefs.com/component/content/5/5?task=view>., (Sep. 2, 2006), 2 pgs.

"The Staple (Biomet's Meniscal Stapler CO2 Gun)", [Online]. Retrieved from the Internet: <URL:http://www.biomet.com/sportsmedicine/getFile.cfm?id=1055&rt=inline>, (1999), 2 pgs.

BIOMET, Sports Medicine, "JuggerKnot and JuggerKnotless Soft Anchor", (2014), 27 pages.

BIOMET Sports Medicine, "JuggerKnot Soft Anchor", (2016), 2 pages.

BIOMET Sports Medicine, "MaxFire Marxmen Meniscal Repair Device Surgical Technique", (2014), 16 pages.

CONMED LINVATEC, "Sequential Meniscal Running Stitch Surgical Technique", (2014), 12 pages.

DEPUY SYNTHES, "Lupine BR and Bioknotless BR Anchors", (2016), 4 pages.

DEPUY SYNTHES Companies, "Omnispan Meniscal Repair System", (Accessed Aug. 11, 2016), 3 pages.

Elliott, M.D., Franklyn, "Plastic Surgery Sutures: Quill Knotless Tissue Closure Device", (Accessed Apr. 1, 2020), 4 pages.

Elliott, M.D., Franklyn, "Quill Knotless Tissue Closure Device", (Accessed Apr. 1, 2020), 3 pages.

Hansen, Juliana, "Covidien A Prospective, Randomized Study to Evaluate Dermal Closure with an Absorbable Barbed Suture", (Oct. 26, 2011), 8 pages.

McCarty, M.D., Eric, "ZipTight Fixation Device with ZipLoop Technology for Chronic Anatomic AC Joint Reconstruction", (2013), 20 pages.

McCarty, M.D., Eric, "Ziptight Fixation System for Acute AC Joint Reconstruction Surgical Technique", (2014), 12 pages.

MITEK Products, "Bioknotless Anchor", (2001), 2 pages.

Robbe, MD, Ruby, et al., "Knotless Based Suture Anchors", Oper Tech Sports Med 12:221-2, (2004), 4 pages.

\* cited by examiner

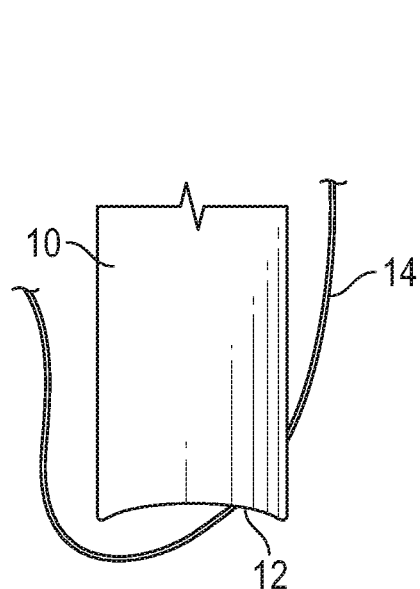
FIG. 1
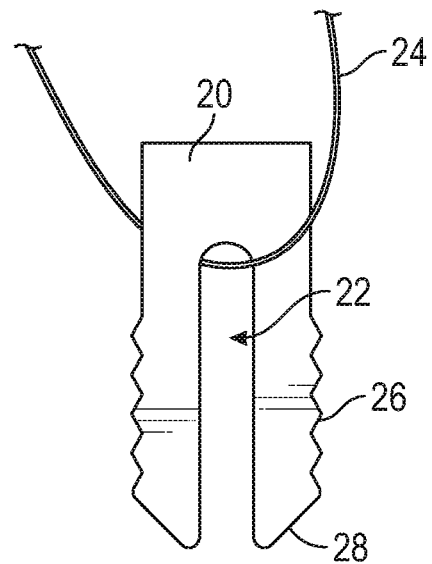
FIG. 2
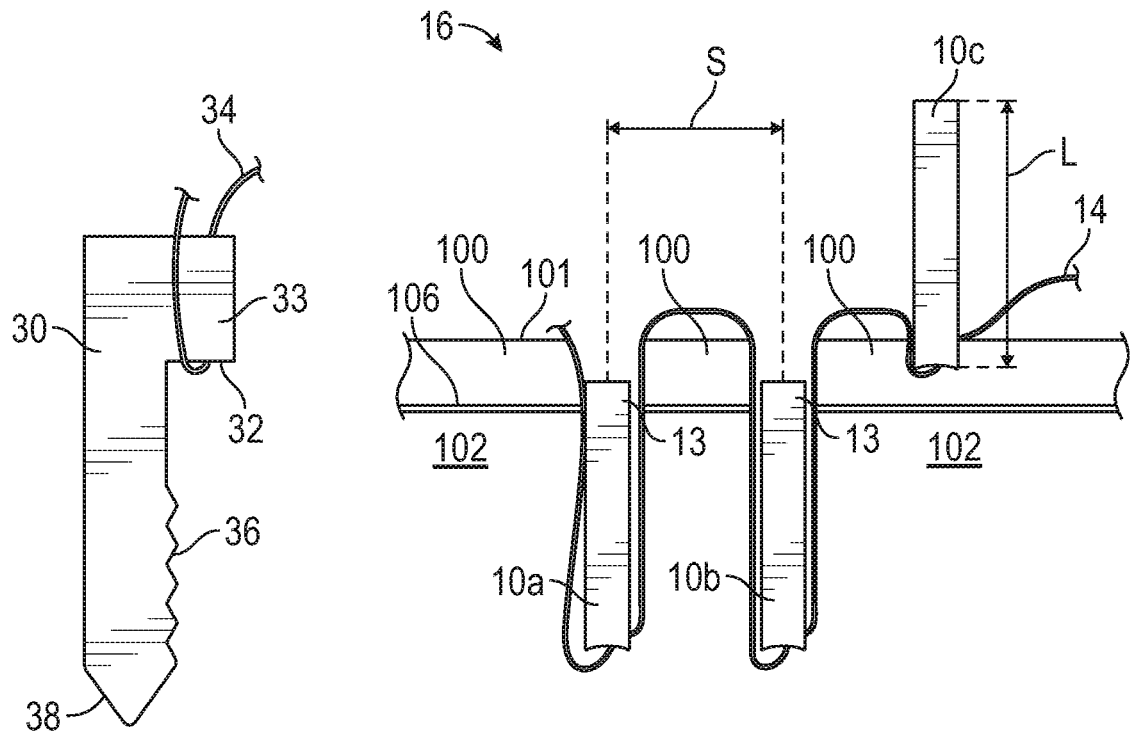
FIG. 3
FIG. 4

METHODS AND SYSTEMS FOR STITCHING SOFT TISSUE TO BONE

CLAIM OF PRIORITY

This application claims the benefit of priority of U.S. Provisional Patent Application Ser. No. 62/419,823, filed on Nov. 9, 2016, and which is herein incorporated by reference in its entirety.

TECHNICAL FIELD

The present application relates to orthopedics, and more particularly, to systems and methods for performing soft tissue repair.

BACKGROUND

Damage to soft tissue, such as one or more tears in the soft tissue, can be common for humans, particularly athletes. Successful repair or reattachment of the soft tissue to the bone can be important, particularly in sports medicine.

Some devices used for soft tissue repair may involve fixation only to the soft tissue and not fixation to both the soft tissue and underlying bone. Other designs can include an anchor that can penetrate into the bone, but those designs may commonly involve drilling to pre-form the hole for the anchor and may involve a plurality of manual steps. One of the challenges can include disruption of the bone during drilling and delivery of the anchor. In designs using sutures, tensioning may be difficult to control.

OVERVIEW

The present inventors recognize, among other things, an opportunity for improved methods and systems for performing soft tissue repair by delivering a suture through the soft tissue and into the bone at two or more fixation points between a first end and a second end of the suture. The two or more fixation points can be spaced apart from each other and connected by the suture, which can be continuous from the first end to the second end. In an example, an implant can be delivered through the soft tissue and bone at each of the two or more fixation points to facilitate delivery of the suture into the bone and fixation of the soft tissue to the bone.

To further illustrate the systems and methods disclosed herein, a non-limiting list of examples is provided here:

Examples according to the present application can include a method of repairing a damaged area of soft tissue. The soft tissue can include one or more tears in the soft tissue and/or detachment of the soft tissue from the underlying bone. The method can include providing a single strand of suture having a first end, a second end opposite the first end, a first portion located between the first end and the second end, and a second portion located between the first portion and the second end, driving a first portion of the single strand through soft tissue and into underlying bone at a first location of the soft tissue in proximity to the damaged area, thereby creating a first suture attachment, and driving a second portion of the single strand through the soft tissue and into the underlying bone at a second location spaced apart from the first location, thereby creating a second suture attachment. In an example, driving the first and second portions of suture into the soft tissue and underlying bone can include using an implant in contact with the respective portion of the suture to drive the respective portion of suture into the soft tissue and underlying bone. The implant can include a feature for securing the suture to the implant as the suture is driven into the soft tissue and underlying bone.

In another example, a method of performing soft tissue repair can include placing a strand of suture on a surface of soft tissue, the strand of suture having a first end and a second end, delivering portions of the strand through the soft tissue and into the bone at two or more fixation points between the first end and the second end of the strand to secure the suture within the soft tissue and bone, and securing the first and second ends of the strand on the surface of the soft tissue. The two or more fixation points can be spaced apart from each other and connected by the portions of the strand extending between the two or more fixation points on the surface of the soft tissue. In an example, the method can further comprise controlling a tension of the suture as the suture is delivered through the soft tissue and into the bone. In an example, at least a portion of the strand of suture can include a braided portion. In such an example, the method can further comprise maintaining a tension of the suture at a first tension during delivery of the suture through the soft tissue and into the bone, and increasing the tension of the suture after delivery of the suture, whereby the braided portion bunches up to aid in fixation of the suture in the bone.

Examples according to the present application can include a system for performing soft tissue repair. The system can comprise a handheld tool and a spool assembly connected to the handheld tool. The handheld tool can be configured to deliver a plurality of implants and a strand of suture into soft tissue and bone to create a plurality of fixation points connected by the strand of suture. The spool assembly (also referred to as a suture assembly) can comprise a reel configured to release portions of the strand as needed during delivery of the plurality of implants. The handheld tool can include a housing, a cartridge configured to releasably store an implant, a tip and a needle. The housing can comprise a piston and an energy source; the piston can be configured to translate axially in the housing when the energy source supplies a force to the piston to move the piston from a rest position to a fired position. The tip can have a connector end and an ejector end, the connector end being open and configured for attachment of the tip to the housing, the tip being hollow from the connector end to the ejector end such that the cartridge is receivable in the tip, the ejector end including one or more features to enable the implant to be delivered from the cartridge and out the ejector end of the tip. The needle can be connected to the piston and configured for axial translation into and through the cartridge and out of the tip when the piston moves from the rest position to the fired position. The spool assembly can be configured to position a portion of the strand in proximity to or in contact with the ejector end of the tip. Translation of the needle through the cartridge and out of the tip can force the implant in the cartridge to be delivered out of the handheld tool and into the soft tissue and bone. As the implant is delivered out of the handheld tool and into the soft tissue and bone, the implant can catch a portion of the strand in proximity to the tip, thereby delivering the suture with the implant into the soft tissue and bone. In an example, the ejector end of the tip can include one or more features for engaging the strand of suture.

These and other examples and features of the present systems and methods will be set forth in part in the following Detailed Description. This Overview is intended to provide non-limiting examples of the present subject matter—it is not intended to provide an exclusive or exhaustive explanation. The Detailed Description below is included to provide further information about the present tooling systems and methods.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 shows an example implant and suture for delivery into soft tissue and bone.

FIG. 2 shows another example implant and suture for delivery into soft tissue and bone.

FIG. 3 shows another example implant and suture for delivery into soft tissue and bone.

FIG. 4 shows a plurality of implants similar to the implant of FIG. 1 being delivered through the soft tissue and secured in the underlying bone.

DETAILED DESCRIPTION

Figure 5:
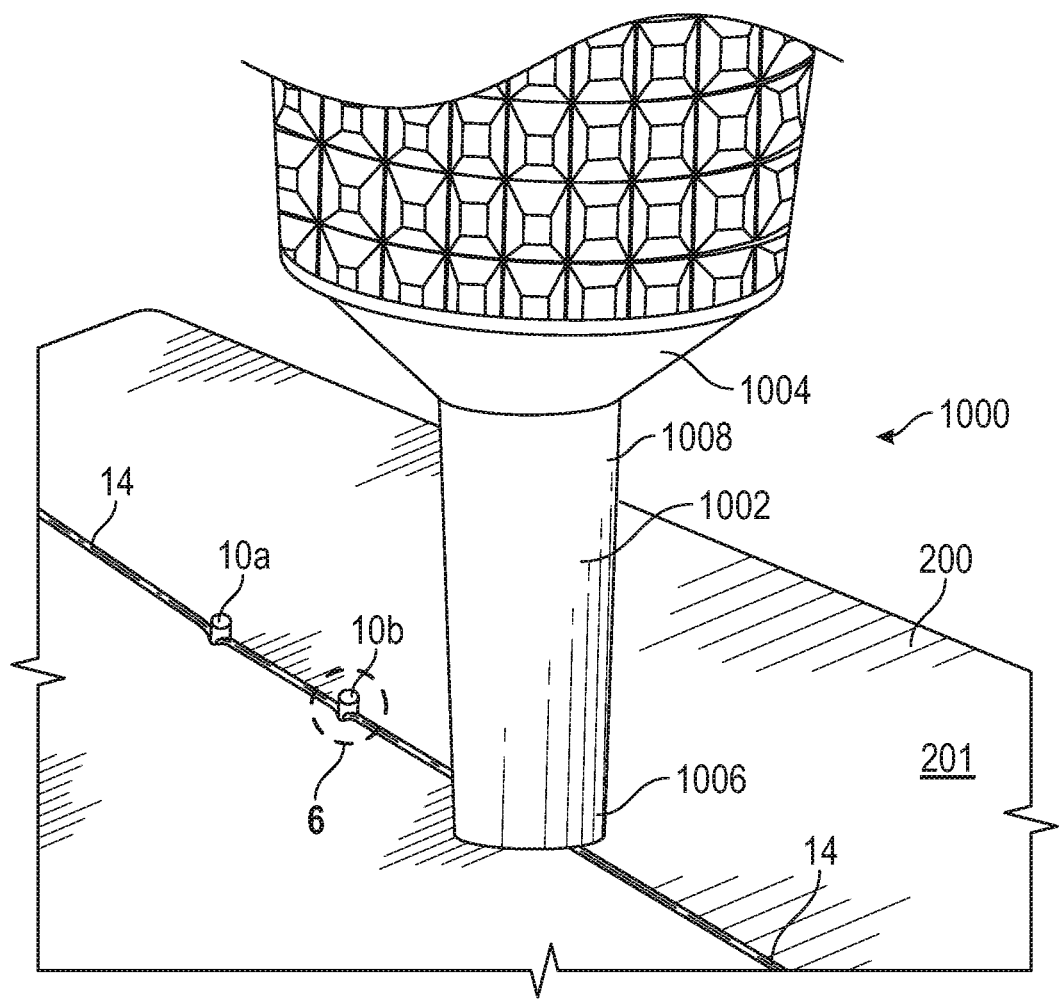
FIG. 5 shows a portion of a handheld tool as the tool is delivering a series of implants through a suture and a substrate underlying the suture.

The present application relates to devices and methods to attach soft tissue to bone with a continuous strand of suture that can be sequentially delivered through tissue and attached to bone. The resulting structure can contain a plurality of discrete fixation points along the length of the suture. The number, location and spacing of the fixation points can be dictated by the surgeon. The present application includes how the continuous line of suture can be caught and drawn into the substrate (tissue and bone). Once inserted, the suture can be locked into bone by an interference fit between either the suture and bone or an implant and bone. The present application also includes how the continuous line of suture can be fed and tensioned as it is driven into the bone. In an example, each anchor point can be described as a "stitch"; each stitch can have a length of suture connecting it to its neighboring stitch. The suture between adjacent stitches can hold down the soft tissue against the underlying bone.

As used herein, the term "continuous strand of suture" can refer to the suture being continuous from a first end to a second end such that a single piece of suture can be used to form the plurality of discrete fixation points. This can be in contrast to a repair system that can include separate suture portions or anchors that are disconnected from one another.

Stitching, as described herein, can represent a shift in how the surgeon approaches surgery for tissue repair and thinks about anchoring soft tissue to bone (no knots), as compared to, and in contrast to, inserting individual anchors and tying knots. Challenges in soft tissue repair can include ensuring that stitching does not damage tissue during insertion, preventing tearing, and providing adequate fixation. The devices and methods of the present application can reduce a number of surgical steps for performing soft tissue repair, and can be used in both arthroscopic and open surgical fields.

In an example, stitching can be performed using one or more implants to grab the suture and drive the suture through the tissue and into the underlying bone at each of the fixation points. In another example, stitching can be performing using just the strand of suture. In an example, the suture can include features to aid in fixation of the suture to the bone. Each of these examples are shown in the figures and described below.

The devices and methods of the present application can be used to achieve an easier and more reproducible surgical technique. This can be due in part to incorporating rapid fixation technology (RFT), developed by Zimmer, Inc., into the devices and methods herein, which can provide an ability to rapidly deliver multiple stitches to repair a soft tissue injury and reattach soft tissue to the underlying bone. Reference is made to U.S. Pat. No. 8,221,433 filed on May 26, 2010 (application Ser. No. 12/787,518), which is incorporated by reference herein. The '433 patent discloses a tool and method for driving a bone pin into fractured bone. The devices and methods of the present application can include use of a device similar to the tool disclosed in the '433 patent and can facilitate soft tissue repair without pre-drilling and with automated, rather than manual, insertion of the suture, and in some examples, the suture and implant in combination. The devices and methods described herein can thus reduce or eliminate operator variability.

FIGS. 1-3 illustrate examples of implants or darts that can be used in conjunction with the strand of suture to aid in securing the suture within the soft tissue and underlying bone. The implants can include one or more features that can help catch the suture or guide the suture into the tissue and bone. The implants can also be referred to herein as anchors. FIG. 1 shows an example implant 10 having a convex end portion 12 configured to engage with a strand of suture 14. The suture 14 can wrap around the implant 10, and a shape of the end portion 12 can aid in ensuring continued engagement between the end portion 12 and suture 14.

In an example, a diameter of the implant 10 can be about 1.7 mm. In other examples, the implant 10 can be larger or smaller than 1.7 mm. In an example, the diameter can range between about 1 and about 3 millimeters. In an example, the diameter can range between about 0.75 and about 6 millimeters.

FIG. 2 shows an example implant 20 having a slot 22 for grabbing a strand of suture 24. It is recognized that the slot 22 can be longer or shorter, relative to an overall length of the implant 20, than what is shown in FIG. 2. In an example, the implant 20 can include additional features, such as teeth 26, to aid in securing the implant 20 to the bone. As also shown in FIG. 2, an exterior shape of the implant 20, such as a tapered tip 28, can help in driving the implant 20 into the bone and ensuring sufficient fixation. FIG. 3 shows an example implant 30 having a step 32 in a side portion 33 of the implant 30 for grabbing or catching a strand of suture 34. As described in regard to FIG. 2, the implant 30 can include additional features, such as teeth 36 or tapered tip 38.

The design of the implants in FIGS. 1-3 can help guide the suture 14 and can reduce the amount of suture used. In an example, the design of the implants in FIGS. 1-3 can promote sliding of the suture, relative to the implant, if desired. Sliding can be used, for example, to prevent overtensioning or to tension the suture after the implants are inserted. If the suture is tensioned after the implants are inserted, in an example, another implant or an anchor can be implanted after the suture is tensioned. In an example, this last implant or anchor can be different from the previously inserted implants and can be designed to prohibit sliding of the suture.

The specific designs of the implants in FIGS. 1-3 are exemplary. Implants or darts having different features and shapes can be used in combination with the strand of suture and are within the scope of the present application.

FIG. 4 illustrates a system 16 for performing soft tissue repair. The system 16 can include the strand of suture 14 of FIG. 1 and a plurality of implants 10a, 10b, and 10c that can be similar to the implant 10 of FIG. 1. In an example, soft tissue 100 can contain one or more tears (not shown in FIG. 4) or one or more detachment sites where the soft tissue 100 is detached from underlying bone 102. The system 16 can be configured to repair the damaged soft tissue 100 or reattach the soft tissue 100, while minimizing disruption to the surrounding tissue 100 and the underlying bone 102. FIG. 4 shows the implants 10a and 10b already in place in the bone 102, and the implant 10c being delivered through the soft tissue 100. The suture 14 can be continuous between the implants 10a, 10b and 10c.

As shown in FIG. 4, the suture 14 can be caught under the end portion 12 of each implant 10a, 10b and 10c. The implants 10a, 10b, and 10c can thus drive the suture 14 into the bone 102 such that the suture 14 can be securely fixed in the bone 102. A fixation strength of the implants 10a, 10b, and 10c can depend, at least in part, on how far each of the implants 10a, 10b and 10c is driven into the bone 102.

The system 16 can facilitate a plurality of fixation points (corresponding to a number of implants 10 delivered) and each pair of adjacent fixation points can be separated by a distance or spacing S (see FIG. 4), which can be variable or constant between each pair of adjacent implants 10. The suture 14 between fixation points can be adjacent to an exterior surface 101 of the soft tissue 100. As further described below, the implants and suture can form any type of pattern or arrangement on the substrate (tissue and bone).

In an example, a top portion 13 of the implants 10 can be above an interior surface 106 of the soft tissue 100 and below the exterior surface 101. As such, the top portion 13 can reside below the exposed surface 101 of the tissue 100. It is recognized that the implants 10a-10c can be implanted into the bone 102 to a depth less than or greater than what is shown in FIG. 4.

In an example, a length L of the implants 10a, 10b and 10c can range between about 3 and about 50 millimeters. In an example, the length L can be greater than 50 millimeters. In an example, the implants 10a, 10b and 10c can have the same length L, as shown in FIG. 4. In another example, the implants 10a, 10b and 10c can have variable lengths relative to each other. In an example, the suture 14 can have a diameter between about 0.3 and about 1.0 millimeter. In an example, the implants 10a, 10b and 10c can have variable diameters relative to each other.

The implants 10 and suture 14 can be formed of any materials suitable for implantation into the tissue 100 and bone 102. Example materials for the implants 10 include, but are not limited to, metals, polymers, biocomposites, resorbable materials, biological materials, or combinations thereof. In an example, the suture 14 can include single or multiple monofilament sutures or multifilament sutures. In an example, the suture 14 can be formed of a low density non-woven mesh.

Figure 6:
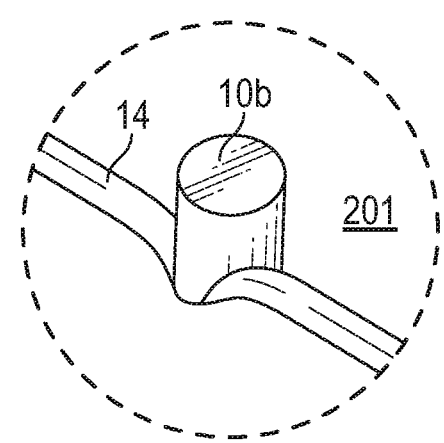
FIG. 6 shows an expanded view of one of the delivered implants and the surrounding suture of FIG. 5.

FIG. 5 shows a portion of a handheld tool 1000 as the handheld tool 1000 delivers a plurality of implants 10 and suture 14 into a substrate 200. The substrate 200 can be representative of the soft tissue and bone shown in FIG. 4. FIG. 5 demonstrates use of the handheld tool 1000 in performing soft tissue repair. FIG. 5 illustrates two implants 10a and 10b secured into the substrate 200 and the handheld tool 1000 in the process of implanting a third implant (not shown). The handheld tool 100 is described further below. FIG. 6 is an expanded view of the implant 10b to better illustrate securement of the implant 10b and suture 14 into the substrate 200.

In an example, as shown in FIG. 5, the suture 14 can be laid down on a surface 201 of the substrate 200 and then the handheld tool 1000 can be generally centered over the suture 14 to deliver the implants 10 into the substrate 200. As a result of delivering the implant 10 into the substrate 200, a portion of the suture 14 under the handheld tool 1000 can be delivered into the substrate 200. In another example, the suture 14 can be spooled using a reel. See for example, a spool or reel shown in FIGS. 12-13, 16-17 and described below.

The handheld tool 1000 can be a rapid fixation tool that can be similar to the tool disclosed in U.S. Pat. No. 8,221,433. In an example, the handheld tool 1000 can include some modifications relative to the tool disclosed in the '433 patent such that the tool can be used in attaching suture to soft tissue and bone or attaching a combination of suture and implants to soft tissue and bone. For instance, the handheld tool 1000 can include a spool assembly or suture assembly (see FIGS. 16-17), which is not included in the tool disclosed in the '433 patent, for the strand of suture that is used in combination with the implants.

The handheld tool 1000, as shown in FIG. 5, can include a tip 1002 and a collar 1004. The collar 1004 can, in an example, be made of metal, and can attach the tip 1002 to the handheld tool 1000. The tip 1002 can have an ejector end 1006 that, when the tool 1000 is in use, can be in close proximity to or contact the surface 201. Examples of the ejector end 1006 of the tip 1002 are shown in FIGS. 9-11C and described below. An opposite end of the tip 1002, a connector end 1008, can be open and the tip 1002 can generally be hollow from the connector end 1008 to the ejector end 1006. A portion of the connector end 1008 can be secured to an interior of the collar 1004, as described below. The tip 1002 can receive a cartridge (see FIG. 8) for temporarily storing a set of implants. The cartridge can contain a plurality of slots extending in a longitudinal direction relative to a length of the cartridge. Each slot in the cartridge can be sized to receive an implant similar to any of the implants shown in FIGS. 1-4. In an example, the cartridge can be configured to store or guide lengths of suture.

Figure 7:
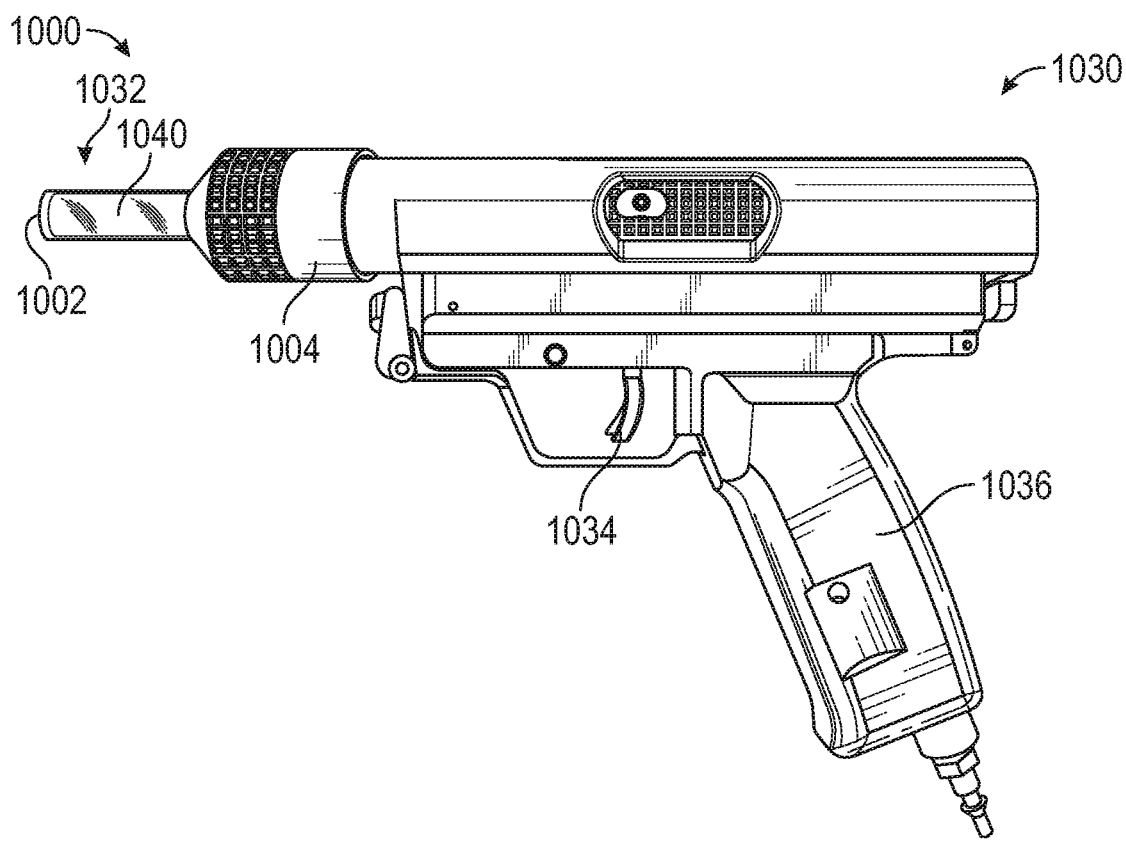
FIG. 7 shows a perspective view of the handheld tool of FIG. 5.

FIG. 7 shows the handheld tool 1000 of FIG. 5. The handheld tool 1000 can include some or all of the features of the tool disclosed in the '433 patent. The tool 1000 can include a first, proximal end 1030 and a second, distal end 1032. The distal end 1032 can include the portions of the tool 1000 shown in FIG. 5—the tip 1002 and the collar 1004. A cartridge 1040 can be contained within the tip 1002. The handheld tool 1000 can also include a trigger 1034 and a handle 1036. In operation, the surgeon can grip the handle 1036 and pull the trigger 1034 to discharge one or more implants, as described below. Although a spool assembly is not shown in the handheld tool 1000 of FIG. 7, it is recognized that the handheld tool 1000 could include a spool assembly that is similar to the spool assembly shown in FIGS. 16 and 17 and described below.

Figure 8:
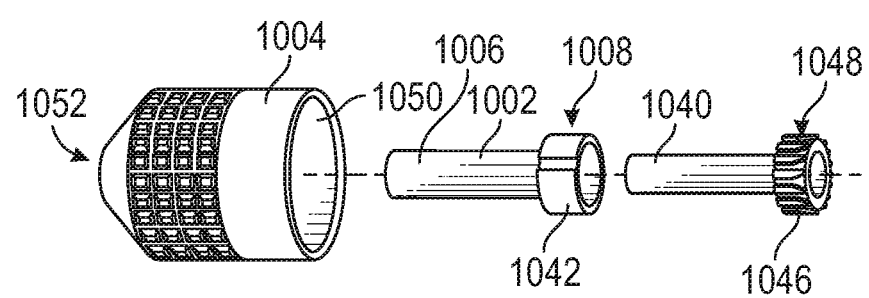
FIG. 8 shows an exploded perspective view of a portion of the handheld tool of FIGS. 5 and 7.

FIG. 8 is an exploded view of the distal end 1032 of the handheld tool 1000, which includes the tip 1002, the collar 1004 and the cartridge 1040. The tip 1002 can include a first feature 1042 at the connector end (or proximal end) 1008 of the tip 1002. The cartridge 1040 can contain a second feature 1046 at a proximal end 1048 of the cartridge 1040 such that the cartridge 1040 can be received within and engage with the tip 1002. The first feature 1042 on the tip 1002 can engage with an interior portion 1050 of the collar 1004 to secure the tip 1002 (and the corresponding cartridge 1040) within the collar 1004.

The tip 1002 and cartridge 1040 can be inserted into the collar 1004 such that the majority of the tip 1002 (and the corresponding collar 1040) can extend through an opening at a distal end 1052 of the collar 1040, while a portion of the connector end 1008 of the tip 1002 (and the collar 1040) can be contained within the interior 1050 of the collar 1004. As described further below in reference to FIGS. 9-11C, the tip 1002 can be placed on or near the soft tissue or bone (see FIG. 5) in preparation for discharging an implant from the cartridge 1040 and driving the implant through the soft tissue and bone.

In an example, the handheld tool 1000 can be pneumatically-powered and can include a piston configured for axial translation inside a barrel located within the handheld tool 1000. The handheld tool 1000 can include a gas supply assembly for supplying pressurized gas as a force to the piston to translate the piston from a rest position to a fired position under the force from the pressurized gas. The piston can be connected to a needle sized for receipt within a passageway of the cartridge 1040. The handheld tool 1000 can be designed such that translation of the piston can cause the needle to move axially and supply sufficient force to the implant in the cartridge 1040 to drive the implant from the cartridge 1040. The implant can thus be fired from the cartridge 1040 through the tip 1002 and into the substrate 201 (see FIG. 5). The needle can then be retracted and the handheld tool 1000 can be moved to the next site on the surface 201 to implant another implant from the cartridge 1040. A design of the handheld tool 1000 can include the ability to control and adjust how far the implant is delivered into the substrate 200.

In an example, the cartridge 1040 can be similar to the cartridge 116 in the '433 patent. A feature can be included in design of the handheld tool 1000 to facilitate rotation of the cartridge 1040 to prepare for delivery of a subsequent implant from the cartridge 1040. In an example, the implants can be preloaded into the cartridge 1040. In an example, the implants can be loaded just prior to the implant procedure.

In another example, the tool 1000 can be spring powered.

A method for performing soft tissue repair using the system shown in FIGS. 5 and 7 can include laying the suture 14 down on a surface 201 of the substrate 200 (manually or using a spool), catching the suture 14 with one of the implants 10 as the implant is ejected from the tip 1002 of the handheld tool 1000 using the needle in the handheld tool 1000, retracting the needle, moving the handheld tool 1000 over to the next intended implant and fixation site, and repeating the steps until the surgeon or other user is satisfied with a number and location of the fixation sites. The method can include cutting the suture 14 at one or both ends once the fixation sites are complete. The ends of the suture 14 can be tied together or individually secured to the surface 201.

One challenge in using suture to repair soft tissue can be managing a tension of the strand 14 during delivery of the implants 10 and suture 14. When the implant 10 is drawn through the soft tissue and into the bone (see FIG. 4), a significant amount of suture 14 can also be drawn into the bone with the implant 10. Without any control during delivery of each implant 10, there can be significant tension to the point that damage can occur—for example, a previously implanted implant 10 can fail or the soft tissue can be cut by the suture 14. The method for performing soft tissue repair can include manual or automated ways of controlling tension. In an example, suture 14 can be spooled on one side of the tip 1002 to create a specific amount of slack in the suture 14 during delivery of each implant 10. Such slack can then be taken up as the next implant is delivered. The steps can be repeated for delivery of each implant 10. The amount of slack can be tailored based in part on a delivery depth of the implant 10. One or more tools or aids can be used with the handheld tool 1000 to create slack in the suture 14 during implant delivery and manage suture tension. In an example, the method for performing soft tissue repair can include managing tension of the overall system of implants and suture, in addition to or as an alternative to managing tension between adjacent implants. In an example, the method can include using more than one type of implant—a first type of implant can allow for suture sliding and a second type of implant can prohibit suture sliding. The second type of implant can lock the suture in place. The second type of implant can be used before or after one or more of the first type of implants are inserted. In an example, a locking implant can be inserted first, the second type of implants can be inserted next, the tension can be manually adjusted and then a final locking implant can be inserted. Any combination or pattern of locking and sliding implants can be used as determined by the surgeon or other user.

FIGS. 9-11C illustrate various examples for a design of the tip 1002 of the handheld tool 1000. FIGS. 9-11A show the tips 1002 oriented facing up with the ejector end 1006 of each tip 1002 visible in FIGS. 9-111A. It is recognized that, when in use and attached to the handheld tool 1000, the tips 1002 face down and the ejector ends 1006 contact, or are in close proximity to, a surface of the substrate for delivery of the one or more implants.

Figure 9:
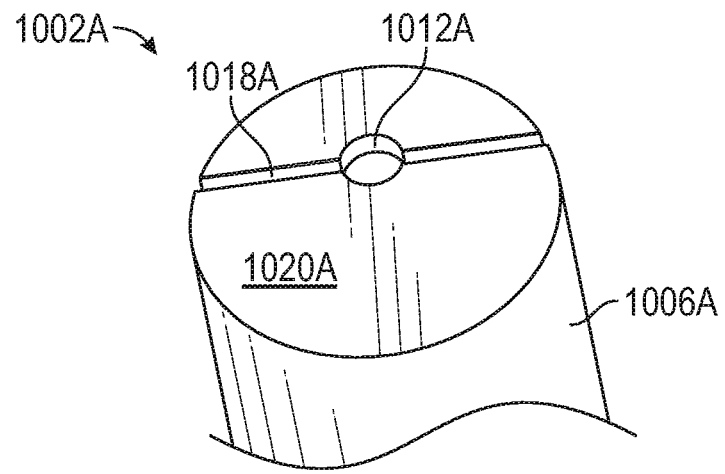
FIG. 9 shows an end portion of an example tip usable in the handheld tool of FIG. 5.

FIG. 9 shows an example tip 1002A having an exit hole 1012A and a horizontally oriented slot 1018A The tip 1002A, and specifically the exit hole 1012A, can be configured within the handheld tool 1000 for alignment with the cartridge that temporarily houses the implants. The exit hole 1012A can be configured such that an implant from inside the handheld tool 1000 can be driven (by the piston and needle inside the handheld tool 1000) out of the handheld tool 1000 through the exit hole 1012A. The exit hole 1012A can be sized and shaped to generally correspond to a size and shape of the implant to be discharged through the hole 1012A. In an example, the exit hole 1012A can be larger than the implant such that the implant can travel through and out the tip 1002A, but not so much larger than the implant in order that the discharge path of the implant can be controlled.

The slot 1018A can be configured to receive a strand of suture, such as the suture 14 shown and described above. The slot 1018A can extend from one end to another end of the tip 1002A (i.e. generally extend a diameter of the tip 1002A) such that the suture can then extend around and up the sides of the tip 1002A. If the handheld tool 1000 in used in combination with a spooling device for the suture, the spooling technique can include passing the suture down a first longitudinal side of the tip 1002A, from a fixed end of the suture, such that the suture can be received in the slot 1018A and then the suture can pass up a second longitudinal side of the tip 1002. The suture can be release from a spooled end of the suture. The slot 1018A can pass through a center of the exit hole 1012A such that the implant, when it is delivered through the hole 1012A, can be generally centered around the underlying suture and effectively drive the suture into the substrate as the implant is driven into the substrate.

In an example shown in FIG. 9, the slot 1018A can be oriented in a generally horizontal direction on a face 1020A of the tip 1002A. The orientation of the slot 1018A can control, at least in part, how the handheld tool 1000 can be oriented by the user, depending on, for example, a desired stitching pattern on the substrate. The orientation can control a hand position of the user during delivery of one or more implants.

Figure 10:
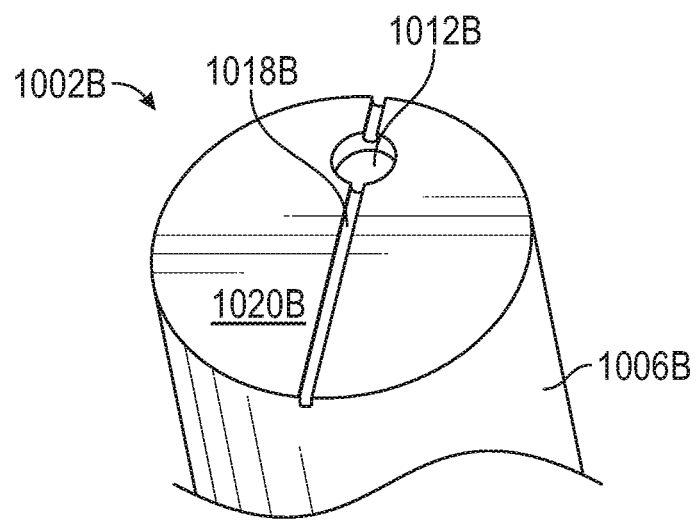
FIG. 10 shows an end portion of another example tip for use in the handheld tool of FIGS. 5 and 7.

FIG. 10 illustrates another example tip 1002B that can be similar to the tip 1002A but the tip 1002B can have a slot 1018B oriented in a generally vertical direction on a face 1020B of the tip 1002A.

Figure 11A:
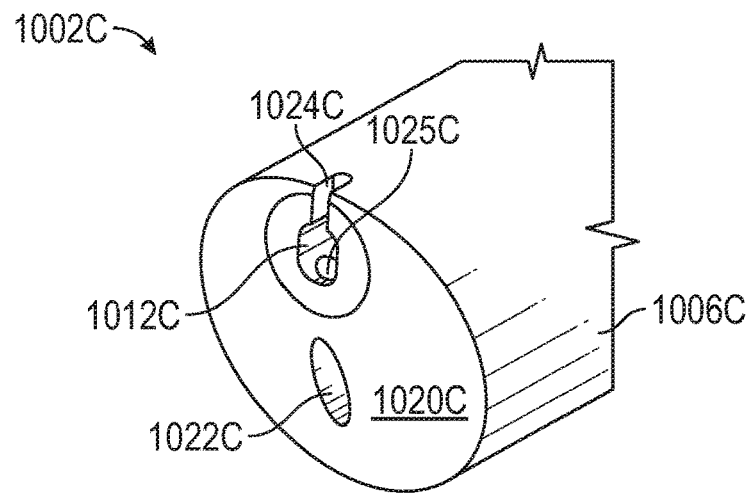
FIG. 11A shows an end portion of another example tip for use in the handheld tool of FIGS. 5 and 7.
Figure 11B:
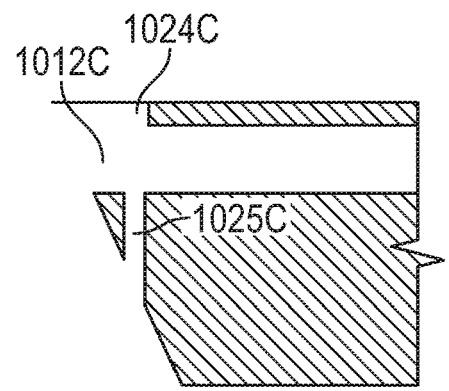
FIG. 11B shows a cross-section view of the end portion of the tip of FIG. 11A.
Figure 11C:
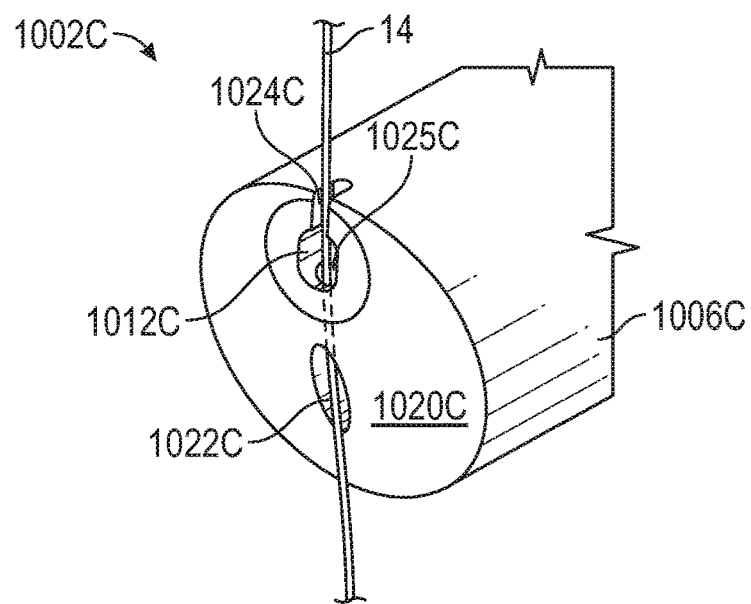
FIG. 11C shows an end portion of the tip of FIG. 11A with a suture secured by the tip.

FIGS. 11A-11C illustrate another example tip 1002C that can include an exit hole 1012C for the implant. As an alternative to a slot extending across a diameter of a face 1020C of the tip 1002C, another hole, designated as a suture hole 1022C, can be aligned with, but spaced from, the exit hole 1012C, and a slot 1024C can be connected to the exit hole 1012C and extend through to the side of the tip 1002C. The tip 1002C can be configured such that the suture strand 14 can be fed through the suture hole 1022C, as shown in FIG. 11C, and up through the slot 1024C via a through-hole 1025C internally located in the end 1006C of the tip 1002C. Alternatively, the strand 14 can be fed first through the slot 1024C and exit hole 102C and then out through the suture hole 1022C. FIG. 11B illustrates a cross-section of the tip 1002C to illustrate the passage of the through-hole 1025C between the exit hole 1012C and the suture hole 1022C. After passing through the exit hole 1012C, the suture 14 can be contained in the slot 1024C. The design of the tip 1006C can facilitate sufficient restraint of the suture 14 and can facilitate control of the suture 14 even if the tool 1006C is drawn away from the tissue. Similar to above for the design in FIGS. 9 and 10, the suture 14 can be generally centered over the exit hole 1012C, which can be generally centered left to right, such that the suture 14 can be centered around the implant when the implant is discharged from inside the handheld tool 1000.

FIGS. 9-11C illustrate examples of the tips 1002 that can be used with the handheld tool 1000. It is recognized that additional designs of the tips 1002 can be used to deliver the implant and suture into the bone. The tips 1002 can be used with a spooled strand or by manually controlling a position of the strand.

Figure 12:
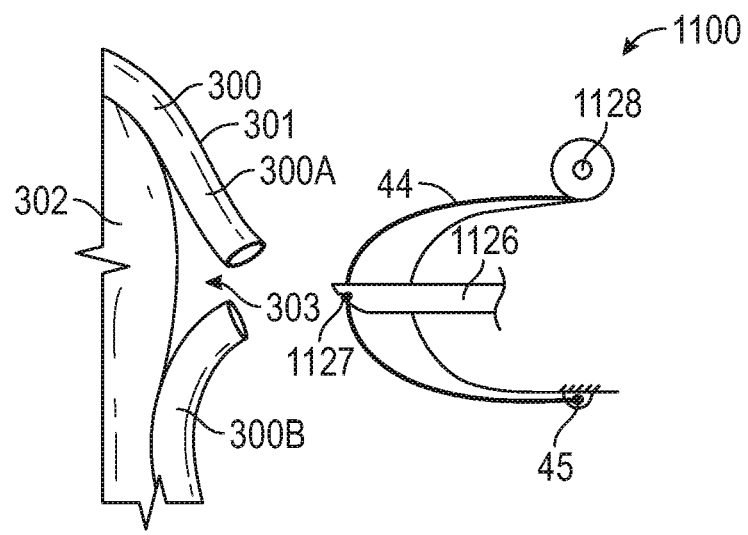
FIG. 12 shows a side view of a portion of a handheld tool before delivery of a spooled suture into damaged soft tissue and underlying bone.
Figure 13:
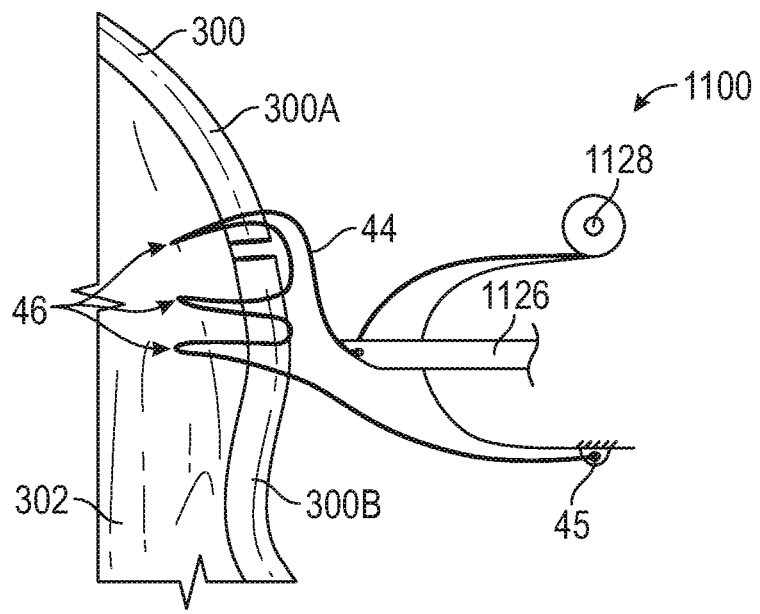
FIG. 13 shows a side view of the handheld tool of FIG. 12 during stitching of the suture into the soft tissue and bone to repair the damaged soft tissue.

FIGS. 12-15 illustrate two examples of performing soft tissue repair using a continuous strand of suture, without one or more implants. FIG. 12 illustrates a tear or break 303 in soft tissue 300 such that first 300A and second 300B portions of the soft tissue 300 are broken apart from each other and each portion 300A and 300B has a flap of tissue 300 peeled back from the underlying bone 302 near the tear 303. A portion of a handheld tool 1100 is shown in FIGS. 12-13 for repairing the damaged soft tissue 300. It is recognized that the handheld tool 1100 can include other components not shown in FIGS. 12-13 and expressly described herein. The handheld tool 1100 can include a suture needle 1126 for implanting suture 44 through the soft tissue 300 and into the underlying bone 302 at multiple fixation points 46 to create a stitching assembly or network. Each fixation point 46 can also be referred to as a stitch. The handheld tool 1100 can be similar to and operate generally as described above for the handheld tool 1000 of FIG. 5. Rather than driving an implant from the cartridge and into the bone as described under FIG. 5 (with the suture captured by the implant), the needle 1126 of FIGS. 12 and 13 can capture the suture 44 directly and drive the suture 44 through the soft tissue 300 and into the bone 302.

The suture 44 can be spooled (similar to bait caster reel) through the needle 1126 with a first end 45 of the suture 44 fixed to the handheld tool 1100 and the rest of the strand 44 wrapped around a spool or reel 1128 of the tool 1100. The needle 1126 can have an open-clevis type feature 1127 for capturing the suture 44 on a forward stroke and releasing the suture 44 on a reverse stroke. Once deposited, the suture 44 can be anchored at each stitch 46 by a 180-degree fold of the suture 44 within a hole created by the needle 1126. It is recognized that other needle designs can be used in addition or as an alternative to the design of the needle 1126.

In the example shown in FIG. 13, three stitches or fixation points 46 are shown. It is recognized that more or less than three stitches can be used to repair the damaged soft tissue 300. In an example, two stitches can be used. In an example, more than three stitches can be used. The number of stitches used for a particular soft tissue repair can depend, in part, on an extent of the damage, an area of the damage and the particular patient's anatomy. A placement of the stitches 46 relative to the tear 303 can be determined by the surgeon before or during the placement of the stitches 46. This is described further below.

A method for performing the soft tissue repair using the system shown in FIGS. 12-13 can include: using the spool 1128 of the tool 1100 to release extra suture so that the suture 44 can be loosely in contact with a surface 301; catching the suture 44 with the feature 1127 of the needle 1126; driving the suture 44 through the soft tissue 300 and into the bone 302; releasing the suture 44; retracting the needle 1126; releasing additional suture 44 from the spool 1128 as needed, moving the handheld tool 1100 over to the next intended site for the next stitch; and repeating the steps until the surgeon or other user is satisfied with a number and location of the stitches in the stitching assembly or network. Last steps of the method can include: releasing a free end from the spool 1128 to create a second end of the suture 44; releasing the fixed end or first end 45 of the suture 44 from the tool 1100; and tacking down the ends of the suture 44 or tying a knot on the surface 301 of the soft tissue 300. The method can include controlling a tension of the suture 44 during creation of each stitch. Such control can include creating a certain amount of slack in the suture 44 prior to driving the suture 44 into the bone 302. One or more tensioning tools can be used, as an alternative or in addition to the spool 1128. In an example, the method can include a twisting action in which a rotational configuration can be used to engage and release the suture 44. In a first configuration, the needle 1126 can engage the suture 44; the tool 1100 can be rotated to a second configuration in which the needle 1126 can release the suture 44. In an example, the method can include multiple needles acting on alternating sequences to aid in the catch/release and/or anchoring steps.

The stitching assembly or network can include two or more fixation points and a placement and pattern of the stitching assembly can vary. For example, the stitching assembly can be defined by each individual surgeon according to anatomy, severity and pathology of the one or more tears 303 or other damage to the soft tissue 300. A benefit of the methods described herein can be that multiple fixation points, each of which can be small, can create a strong stitching network, while minimizing disruption to the tissue 300 and bone 302. Knot tying can also be reduced or eliminated. For example, a knot does not have to be tied at each fixation point. The stitching pattern can depend, in part, on a location of the soft tissue in the body. In an example, the stitching pattern can include fixation points through bone only (in an area in which soft tissue does not cover a portion of the surrounding bone) and fixation points through the soft tissue and bone. The suture between each of the fixation points can extend across the surface of the bone or tissue and connect each stitch or fixation point to each other.

Figure 14:
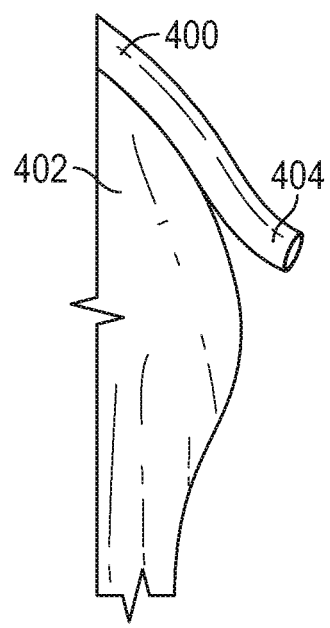
FIG. 14 shows a side view of soft tissue detached from the underlying bone.

FIG. 14 illustrates another example of soft tissue damage. In the example shown in FIG. 14, an end portion 404 of soft tissue 400 can become detached from underlying bone 402. Suture 44 can be delivered through the soft tissue 400 and into the bone 402 at two or more fixation points 46A to reattach the end portion 404 to the underlying bone 402. In an example, the suture 44 can also be delivered through the bone 402 adjacent to the end portion 404 of the soft tissue 400 to create one or more fixation points 46B through the bone 402. The fixation points 46B can help secure the suture 44 through the soft tissue 400 at the fixation points 46A. In another example, the fixation points 46B can be excluded. As similarly described above, a number and placement of fixation points 46A and 46B can vary and can be determined by the surgeon.

Although not shown in FIGS. 12-15, in an example, the method described above and shown in FIGS. 12-15 can include implanting a mesh material between the soft tissue 300 or 400 and bone 302 or 402 and stitching through the mesh to attach the mesh (between the soft tissue 300, 400 and bone 302, 402) using the suture 44. Similarly, in an example, the method described above and shown in FIGS. 12-15 can include implanting a mesh material on an exterior surface 301 or 401 of the soft tissue 300 or 400, respectively, and using the needle 1126 to drive the suture 44 through the mesh and the underlying soft tissue 300, 400 and bone 302, 402. The mesh material can be used, for example, if there is a concern about the suture 44 tearing the soft tissue 300, 400.

In another example, the mesh material can supply the suture and a separate strand of suture (like strand 44) can be excluded. In such an example, the mesh material can be inserted between the soft tissue 300, 400 and bone 302, 402, or the mesh material can be placed on the exterior surface 301, 401 of the soft tissue 300, 400. The needle 1126 can be used to puncture the mesh material and drag a portion of the mesh material into the bone 302, 402 (and through the soft tissue 300, 400 if the mesh is on top of the soft tissue 300, 400). As such, the portion of the mesh going through the bone 302, 402 (and soft tissue 300, 400, if applicable) can function similar to the suture strand 44.

In an example, after the stitching assembly is complete, the method can include cutting away any excess, unstitched mesh material. As similarly described above, this type of design can permit a large number of small implants to be implanted deep into the bone. The number of implant (fixation points) or stitches can be based in part on surgeon needs or preferences. This type of design may not require any anterior/posterior or medial/lateral stitching pattern.

Figure 16:
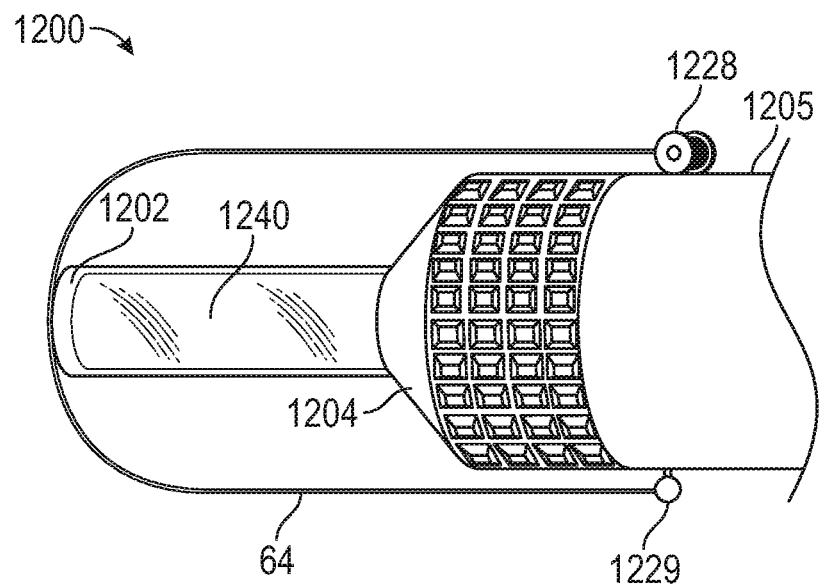
FIG. 16 shows a portion of a handheld tool having an externally-attached spool assembly.
Figure 17:
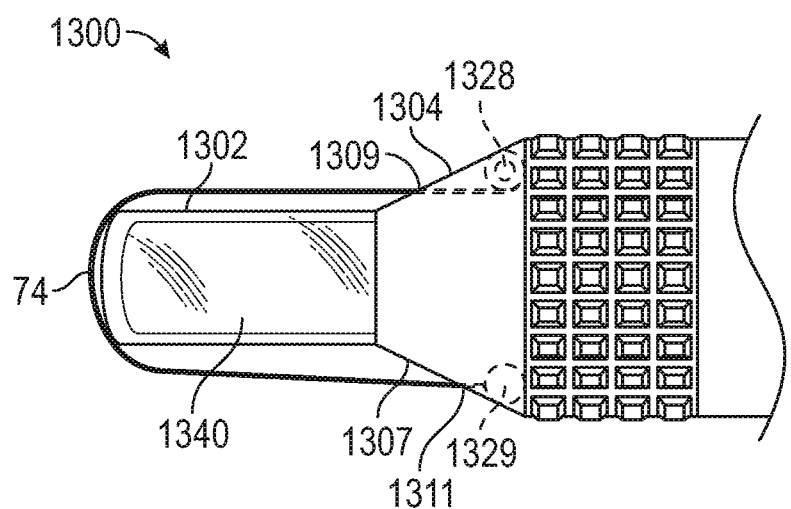
FIG. 17 shows a portion of a handheld tool having an internally-attached spool assembly.

FIGS. 16 and 17 show two examples of a distal portion of handheld tools 1200 and 1300 that each include a spool assembly. FIG. 16 is an example of an external spool assembly (fixed to an exterior of the handheld tool 1200) and FIG. 17 is an example of an internal spool assembly (fixed within an interior of the handheld tool 1300). Although only a distal portion of each of the handheld tools 1200 and 1300 is shown in FIGS. 16 and 17, it is recognized that an overall design of the handheld tools 1200 and 1300 can be similar to the handheld tool 1000 described above and shown in FIGS. 5 and 7.

The handheld tool 1200 of FIG. 16 can include the same components as described above in reference to FIGS. 7 and 8, which includes a collar 1204, a tip 1202 and a cartridge 1240 received within the tip 1202. The handheld tool 1200 can include a spool assembly having a fixation feature 1229 and a spool 1228, both of which can be attached to or fixed to an exterior 1205 of the collar 1204 on opposing sides. A strand of suture 64 can be fixed to the fixation feature 1229, extend around the end of the tip 1202 and then be spooled or wrapped on the spool 1228. In an example, the fixation feature 1229 can be an eyelet or some other component that the strand 64 can be tied to or otherwise fixed to. During the method of performing the soft tissue repair, as described above, additional suture 64 can be released from the spool 1228 as needed or desired. As described above, the tip 1202 can include a slot or other feature for engaging the suture 64.

FIG. 17 shows a side view of a handheld tool 1300 having a collar 1304, a tip 1302 and a cartridge 1340. The handheld tool 1300 is similar to the tool 1200 of FIG. 16, but includes a spool 1328 and a fixation feature 1329, both for a suture strand 74, which are attached to an interior of the collar 1304. (These internally located features are shown in broken lines or in phantom in FIG. 17.) As similarly described above, the fixation feature 1329 can include an eyelet or other component that can attach to an interior wall of the collar 1304; one end of the strand 74 can be tied to or otherwise fixed to the fixation feature 1329.

A distal portion 1307 of the collar 1304, which can have a conical shape, can include two openings 1309 and 1311 configured for the strand 74 to pass through. A size of each of the openings 1309 and 1311 can be designed such that the respective opening 1309 or 1311 is large enough that the strand 74 can easily move through the opening (as the strand 74 is unwound from the spool 1328) but small enough that the respective opening 1309 or 1311 can help control the strand 74 such that the strand 74 remains engaged with or in proximity to the end of the tip 1302.

It is recognized that additional designs or features of a suture or spool assembly can be used in addition to or as an alternative to the designs in FIGS. 16 and 17, in order to provide a strand of suture that can be implanted through the soft tissue and bone as the implant is discharged from the handheld tool. For example, different types of fixation features can be used to fix one end of the suture to the collar, different types of spooling designs can be used to store the suture and provide the ability to unwind additional suture, and the spool or fixation feature can be attached at different regions of the handheld tool than what is shown in FIGS. 16 and 17. In an example, either of the spool or the fixation feature can be internally attached to the housing of the tool and the other of the spool or the fixation feature can be externally attached.

Figure 18:
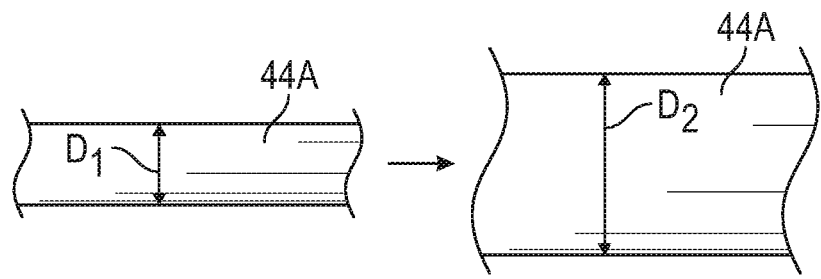
FIG. 18 shows an example suture before and after swelling.
Figure 19:
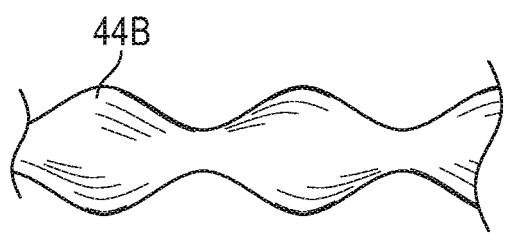
FIG. 19 shows an example suture having a varying diameter over a length of the suture.
Figure 20:
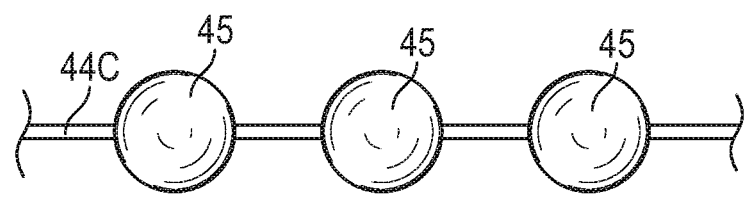
FIG. 20 shows an example suture having a plurality of beads.

FIGS. 18-20 show example sutures 44 usable in the methods and systems described herein. Suture fixation can be accomplished by interference with the hole created by a needle. Fixation can be further facilitated by features or properties of the suture 44 itself. FIG. 18 illustrates an example suture 44A. The strand 44A can have a first diameter D1 when the suture 44A is implanted. The suture 44A can have a second diameter D2 after some period of time, due to expansion or swelling of the material used to form the suture 44A. Swelling of the suture 44A can promote an interference fit of the suture 44A within the hole of the bone. In an example, the suture 44A can be formed of collagen.

Figure 15:
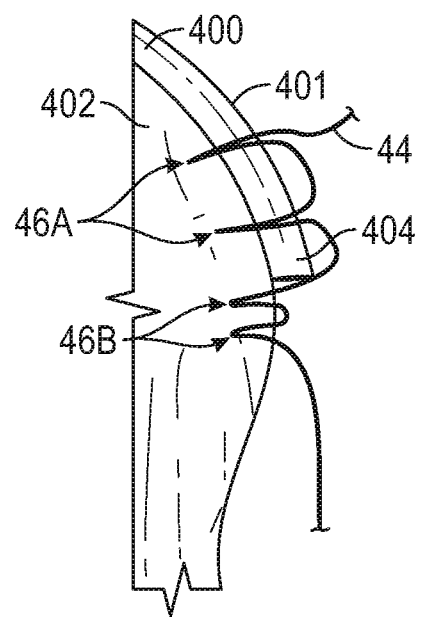
FIG. 15 shows a side view of the soft tissue and bone of FIG. 14 after suture is stitched into the soft tissue and bone to repair the detached soft tissue.

FIGS. 19 and 20 illustrate geometrical variations in the sutures 44B and 44C that can aid in fixation within the bone and tissue. The strand 44B of FIG. 19 can have a varying diameter across a length of the strand. The varying diameter can be in a pattern, as shown in FIG. 19, or the varying diameter can be random across the length of the strand 44B. The strand 44C of FIG. 20 can include a plurality of beads 45 arranged across a length of the strand 44C. A size of the beads 45 as shown in FIG. 20 may be exaggerated for clarity. It is recognized that a size of the beads 45 may actually be smaller relative to a diameter of the strand 44C. FIGS. 14-16 illustrate examples of material properties and structures that can be used to create fixation features for the suture 44. It is recognized that other features can be included as an alternative or in addition to the specific examples shown herein.

Figure 21:
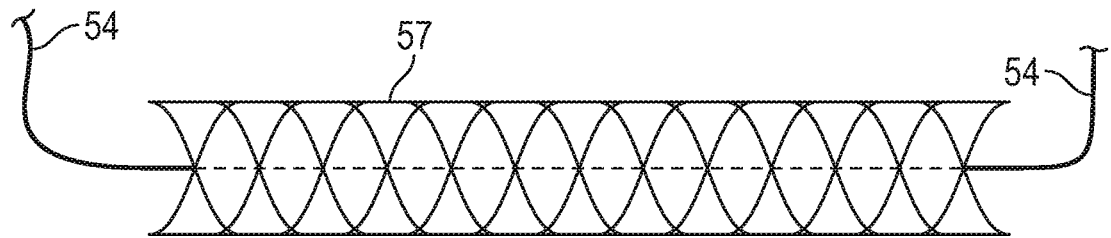
FIG. 21 shows an example suture received within a braided structure.
Figure 22:
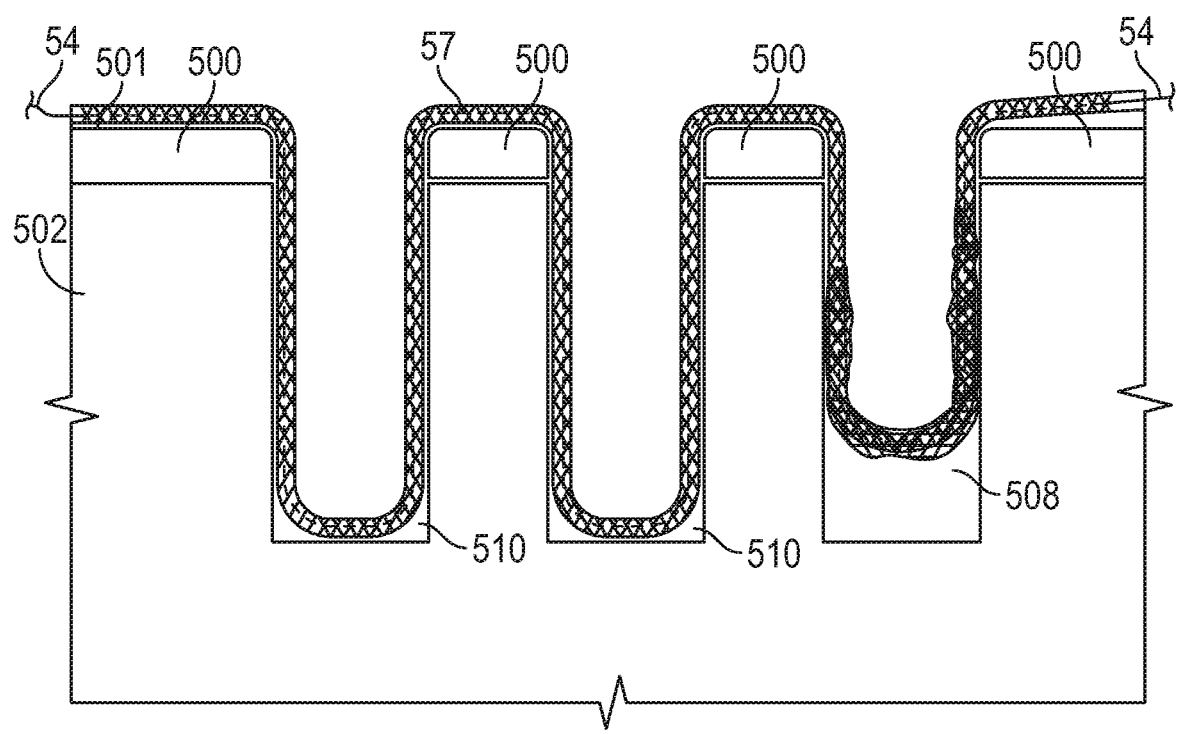
FIG. 22 shows the suture of FIG. 21 implanted into tissue and bone, and after a portion of the suture is tensioned.

FIGS. 21 and 22 illustrate an example of performing soft tissue repair using a braid of suture 57 having a tensioning suture 54 running through a core of the braided suture 57. The braided suture 57 can be positioned on a top surface 501 of soft tissue 500 of FIG. 22. A punch, or a similar device, can be used to drive the braided suture 57 into bone 502 underlying the soft tissue 500, resulting in a loop of braided suture 57 in each hole 508, 510, 512 formed in the bone 502 and tissue 500, by the punch or other tooling. The tensioning suture 54 can be pulled, thereby causing the braid 57 to bunch up as demonstrated in the hole 508. The bunching of the braid 57 in the hole 508 can facilitate fixation of the braid 57 within the bone 502. In an example, the portion of the braids 57 in each of the holes 508, 510, and 512 can be bunched sequentially or simultaneously as portions of the tensioning suture 54 are pulled. Once bunching is complete, the ends of the tensioning strand 54 can be tied off or tacked down. In the example shown in FIG. 22, the braided suture 57 covers all of the tensioning suture 54. In other examples, disconnected portions of the braided suture 57 can be used and the suture 54 can be exposed between portions of the braided suture 57, such as, for example, between the holes 508, 510 and 512.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The present application provides for the following exemplary embodiments or examples, the numbering of which is not to be construed as designating levels of importance:

Example 1 provides a method of repairing a damaged area of soft tissue comprising providing a single strand of suture having a first end, a second end opposite the first end, a first portion located between the first end and the second end, and a second portion located between the first portion and the second end. The method can further comprise driving a first portion of the single strand through soft tissue and into underlying bone at a first location of the soft tissue in proximity to the damaged area, thereby creating a first suture attachment, and driving a second portion of the single strand through the soft tissue and into the underlying bone at a second location spaced apart from the first location, thereby creating a second suture attachment.

Example 2 provides the method of Example 1 optionally further comprising creating additional suture attachments spaced apart from each other and spaced apart from the first and second suture attachments.

Example 3 provides the method of Example 1 or 2 optionally configured such that driving the first and second portions of suture into the soft tissue and underlying bone includes using an implant in contact with the respective portion of the suture to drive the respective portion of suture into the soft tissue and underlying bone.

Example 4 provides the method of Example 3 optionally configured such that the suture wraps around a portion of the implant prior to driving the respective portion of suture into the soft tissue and underlying bone.

Example 5 provides the method of Example 3 or 4 optionally configured such that the implant is temporarily stored inside a housing of a handheld tool configured to drive the implant from the housing and into the soft tissue and underlying bone.

Example 6 provides the method of any of Examples 1-5 optionally further comprising storing the strand of suture on a spool prior to driving the respective portion of suture into the soft tissue and underlying bone, and releasing portions of the strand from the spool to create slack before the next suture attachment is created.

Example 7 provides the method of any of Examples 1-6 optionally further comprising controlling a tension of the strand as the suture attachments are created.

Example 8 provides the method of any of Examples 1-7 optionally further comprising, after creating the first and second suture attachments, securing the first and second ends of the strand on a surface of the soft tissue.

Example 9 provides the method of Example 8 optionally configured such that securing the first and second ends of the strand on the surface of the soft tissue includes at least one of tacking one or both of the ends to the surface and forming a knot on the surface.

Example 10 provides a method of performing soft tissue repair comprising placing a strand of suture on a surface of soft tissue, the strand of suture having a first end and a second end, delivering portions of the strand through the soft tissue and into the bone at two or more fixation points between the first end and the second end of the strand to secure the suture within the soft tissue and bone, and securing the first and second ends of the strand on the surface of the soft tissue. The two or more fixation points can be spaced apart from each other and connected by the portions of the strand extending between the two or more fixation points on the surface of the soft tissue.

Example 11 provides the method of Example 10 optionally configured such that delivering the suture through the soft tissue and into the bone at two or more fixation points includes driving an implant into the soft tissue and bone at each of the two or more fixation points, each implant secured to the suture at each of the two or more fixation points.

Example 12 provides the method of Example 11 optionally configured such that the implant includes a feature for securing the suture to the implant.

Example 13 provides the method of Example 10 optionally configured such that at least a portion of the strand of suture includes a braided portion and the method optionally further comprises maintaining a tension of the suture at a first tension during delivery of the suture through the soft tissue and into the bone and increasing the tension of the suture after delivery of the suture, whereby the braided portion bunches up to aid in fixation of the suture in the bone.

Example 14 provides the method of any of Examples 10-13 optionally further comprising controlling a tension of the suture as the suture is delivered through the soft tissue and into the bone.

Example 15 provides a system for performing soft tissue repair comprising a handheld tool and a spool assembly connected to the handheld tool. The handheld tool can be configured to deliver a plurality of implants and a strand of suture into soft tissue and bone to create a plurality of fixation points connected by the strand of suture. The spool assembly can comprise a reel configured to release portions of the strand as needed during delivery of the plurality of implants. The handheld tool can comprise a housing comprising a piston and an energy source. The piston can be configured to translate axially in the housing when the energy source supplies a force to the piston to move the piston from a rest position to a fired position. The housing can further comprise a cartridge configured to releasably store an implant, and a tip having a connector end and an ejector end. The connector end can be open and configured for attachment of the tip to the housing, the tip being hollow from the connector end to the ejector end such that the cartridge is receivable in the tip, and the ejector end including one or more features to enable the implant to be delivered from the cartridge and out the ejector end of the tip. The housing can further comprise a needle connected to the piston and configured for axial translation into and through the cartridge and out of the tip when the piston moves from the rest position to the fired positions. The spool assembly can be configured to position a portion of the strand in proximity to or in contact with the ejector end of the tip. Translation of the needle through the cartridge and out of the tip can force the implant in the cartridge to be delivered out of the handheld tool and into the soft tissue and bone. As the implant is delivered out of the handheld tool and into the soft tissue and bone, the implant can catch a portion of the strand in proximity to the tip, thereby delivering the suture with the implant into the soft tissue and bone.

Example 16 provides the system of Example 15 optionally configured such that the ejector end of the tip includes an exit hole for discharging the implant from the handheld device.

Example 17 provides the system of Example 15 or 16 optionally configured such that the ejector end of the tip includes a slot configured to receive the portion of the strand in contact with the ejector end.

Example 18 provides the system of any of Example 15-17 optionally configured such that the cartridge comprises a plurality of slots, each slot configured to store an implant.

Example 19 provides the system of any of Example 15-18 optionally configured such that the spool assembly comprises a fixed portion located on a first side of the housing, the fixed portion configured to secure a first end of the strand during operation of the handheld tool. The reel can be located on a second side of the housing opposite the first side such that the strand extends from the fixed portion to the reel and under the tip of the handheld tool.

Example 20 provides a system or method of any one or any combination of Examples 1-19, which can be optionally configured such that all steps or elements recited are available to use or select from.

Various aspects of the disclosure have been described. These and other aspects are within the scope of the following claims.

The claimed invention is:

1. A method of repairing a damaged area of soft tissue, the method comprising:
   providing a single strand of suture having a first end, a second end opposite the first end, a first portion located between the first end and the second end, and a second portion located between the first portion and the second end;
   releasably storing the single strand of suture on a spool of a handheld tool, the handheld tool configured to temporarily store a first implant and a second implant inside the handheld tool;
   driving a first portion of the single strand through soft tissue and into underlying bone at a first location of the soft tissue in proximity to the damaged area by driving the first implant from the handheld tool and into the soft tissue and underlying bone, thereby creating a first suture attachment; and
   driving a second portion of the single strand through the soft tissue and into the underlying bone at a second location spaced apart from the first location by driving the second implant from the handheld tool and into the soft tissue and underlying bone, thereby creating a second suture attachment,
   wherein the first and second implants are ejected from an ejector end of the handheld tool, and the ejector end includes a slot formed in an end face of the ejector end and extending across a diameter of the end face of the ejector end, and
   wherein the single strand wraps around the ejector end of the tool such that the first and second portions of the single strand are received in the slot prior to driving each of the first and second portions of the single strand through the soft tissue and into the underlying bone.

2. The method of claim 1 further comprising:
   creating additional suture attachments spaced apart from each other and spaced apart from the first and second suture attachments.

3. The method of claim 2 further comprising;
   driving additional portions of suture into the soft tissue and underlying bone using additional implants, each additional implant in contact with the respective additional portion of the suture to drive the respective portion of suture into the soft tissue and underlying bone.

4. The method of claim 1 further comprising:
   releasing portions of the strand from the spool to create slack before the next suture attachment is created.

5. The method of claim 1 further comprising:
   controlling a tension of the strand as the suture attachments are created.

6. The method of claim 1 further comprising:
   after creating the first and second suture attachments, securing the first and second ends of the strand on a surface of the soft tissue.

7. The method of claim 6 wherein securing the first and second ends of the strand on the surface of the soft tissue includes at least one of tacking one or both of the ends to the surface and forming a knot on the surface.

8. A method of performing soft tissue repair, the method comprising:
   providing a handheld device configured to drive one or more implants from inside the handheld device and into soft tissue and underlying bone;
   wrapping a strand of suture around an ejector end of the handheld device;
   releasably receiving the strand of suture through a slot formed in and end face of the ejector end of the handheld device wherein the slot extends across a diameter of the end face of the ejector end:
   placing the strand of suture on a surface of soft tissue, the strand of suture having a first end and a second end;
   driving a first implant and a second implant from inside the handheld device through the soft tissue and into an underlying bone at first and second fixation points between the first end and the second end of the strand to secure the suture within the soft tissue and bone; and
   securing the first and second ends of the strand on the surface of the soft tissue,
   wherein the two or more fixation points are spaced apart from each other and connected by the portions of the strand extending between the two or more fixation points on the surface of the soft tissue.

9. The method of claim 8 wherein the implant includes a feature for securing the suture to the implant.

10. The method of claim 8 wherein at least a portion of the strand of suture includes a braided portion and the method further comprises:
    maintaining a tension of the suture at a first tension during delivery of the suture through the soft tissue and into the bone; and
    increasing the tension of the suture after delivery of the suture; whereby the braided portion bunches up to aid in fixation of the suture in the bone.

11. The method of claim 8 further comprising:
    storing the strand of suture on a spool of the handheld device, prior to securing the suture within the soft tissue and bone.

* * * * *

UNITED STATES PATENT AND TRADEMARK OFFICE
CERTIFICATE OF CORRECTION

PATENT NO. : 10,966,704 B2  
APPLICATION NO. : 15/808547  
DATED : April 6, 2021  
INVENTOR(S) : Lozier et al.

Page 1 of 1

It is certified that error appears in the above-identified patent and that said Letters Patent is hereby corrected as shown below:

In the Claims

In Column 17, Line 54, in Claim 3, delete "comprising;" and insert --comprising:-- therefor In Column 18, Line 26, in Claim 8, delete "and" and insert --an-- therefor In Column 18, Line 27, in Claim 8, delete "device" and insert --device,-- therefor In Column 18, Line 28, in Claim 8, delete "end:" and insert --end;-- therefor In Column 18, Line 51, in Claim 10, delete "suture;" and insert --suture,-- therefor Signed and Sealed this  
First Day of June, 2021

Drew Hirshfeld  
*Performing the Functions and Duties of the*  
*Under Secretary of Commerce for Intellectual Property and*  
*Director of the United States Patent and Trademark Office*